US00PP27680P2

(12) United States Plant Patent
Trees

(10) Patent No.: US PP27,680 P2
(45) Date of Patent: Feb. 21, 2017

(54) ***ROSA* PLANT NAMED 'SFROSA159'**

(50) Latin Name: *Rosa hybrida*
Varietal Denomination: SFROSA159

(71) Applicant: Scott C. Trees, Arroyo Grande, CA (US)

(72) Inventor: Scott C. Trees, Arroyo Grande, CA (US)

(73) Assignee: SUNRISE FARM FLOWERS, LLC, Arroyo Grande, CA (US)

( * ) Notice: Subject to any disclaimer, the term of this patent is extended or adjusted under 35 U.S.C. 154(b) by 189 days.

(21) Appl. No.: 14/121,319

(22) Filed: Aug. 19, 2014

(51) Int. Cl.
*A01H 5/02* (2006.01)

(52) U.S. Cl.
USPC ..... Plt./107

(58) Field of Classification Search
USPC ..... Plt./107
See application file for complete search history.

*Primary Examiner* — Keith Robinson
(74) *Attorney, Agent, or Firm* — Penny J. Aguirre

(57) ABSTRACT

A new cultivar of shrub rose, 'SFROSA159', that is characterized by its upright, compact plant habit, its single flowers with five large, flat petals and borne in clusters of five to eight, its continuous flowering throughout the season, its flowers that are saturated hot pink in color and nearly non-fading, its glossy dark green foliage, its cold hardiness at least to U.S.D.A. Zone 6, and its tolerance to powdery mildew and rust in California trials and tolerance to black spot in trials in the Midwest.

2 Drawing Sheets

Botanical classification: *Rosa hybrida.*
Variety denomination: 'SFROSA159'.

BACKGROUND OF THE INVENTION

The present invention relates to a new and distinct cultivar of *Rosa hybrida*. The new cultivar will be referred to hereafter by its cultivar name, 'SFROSA159'. 'SFROSA159' is a new cultivar of shrub rose grown for use as a landscape shrub.

The new cultivar of shrub rose is a selection from a controlled breeding program conducted by the Inventor in Arroyo Grande, Calif. with an objective to create new shrub rose cultivars with disease resistance, ever blooming habits, and unique brightly colored flowers that can be readily propagated on their own roots.

The new variety of shrub rose, 'SFROSA159', was selected by the Inventor from amongst seedlings derived from a cross made in July of 2009 between plants of the cultivar, 'Meizmea' (U.S. Plant Pat. No. 20,175) as both the female and male parent. 'SFROSA159' was selected as a single unique plant in May of 2010.

Asexual propagation of the new cultivar was first accomplished by stem cuttings in Arroyo Grande, Calif. in August of 2010 by the Inventor. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'SFROSA159' as a new and unique cultivar of shrub rose.

1. 'SFROSA159' exhibits an upright, compact plant habit.

2. 'SFROSA159' exhibits large single flowers with five flat petals and borne in clusters of five to eight.
3. 'SFROSA159' exhibits continuous flowering throughout the season.
4. 'SFROSA159' exhibits flowers that are a saturated hot pink color and nearly non-fading.
5. 'SFROSA159' exhibits glossy dark green foliage.
6. 'SFROSA159' exhibits cold hardiness at least to U.S.D.A. Zone 6.
7. 'SFROSA159' exhibits tolerance to powdery mildew and rust in California trials and tolerance to black spot in trials in the Midwest.

'SFROSA159' can be distinguished from plants of its parent, shrub rose, 'Meizmea'. 'Meizmea' is similar to 'SFROSA159' in having single flowers with five petals and in having disease resistance to black spot. 'Meizmea' differs from 'SFROSA159' in having flowers that are bicolored red and white, in having flowers that are smaller in diameter with smaller curled petals, in having flower clusters with more flowers, in having a more branched plant habit, in having leaflets that are smaller in size and light green in color, and in having flower flushes throughout the season rather than continuous blooming. 'SFROSA159' can be most closely compared to the shrub rose cultivar 'WEKphorn' (U.S. Plant Pat. No. 22,856). 'WEKphorn' is similar to 'SFROSA159' in having bright hot pink flowers. 'WEKphorn' differs from 'SFROSA159' in having flowers that are smaller in diameter, four to eight petals, fade to a light pink color, and in having a more branched plant habit.

BRIEF DESCRIPTION OF THE DRAWINGS

The accompanying colored photographs illustrate the overall appearance and distinct characteristics of the new shrub rose. The photographs were taken of 2 year-old plants as grown outdoors in a one-gallon container in Arroyo Grande, Calif.

The photograph in FIG. 1 provides a side view of the plant habit of 'SFROSA159'.

Figure 1:
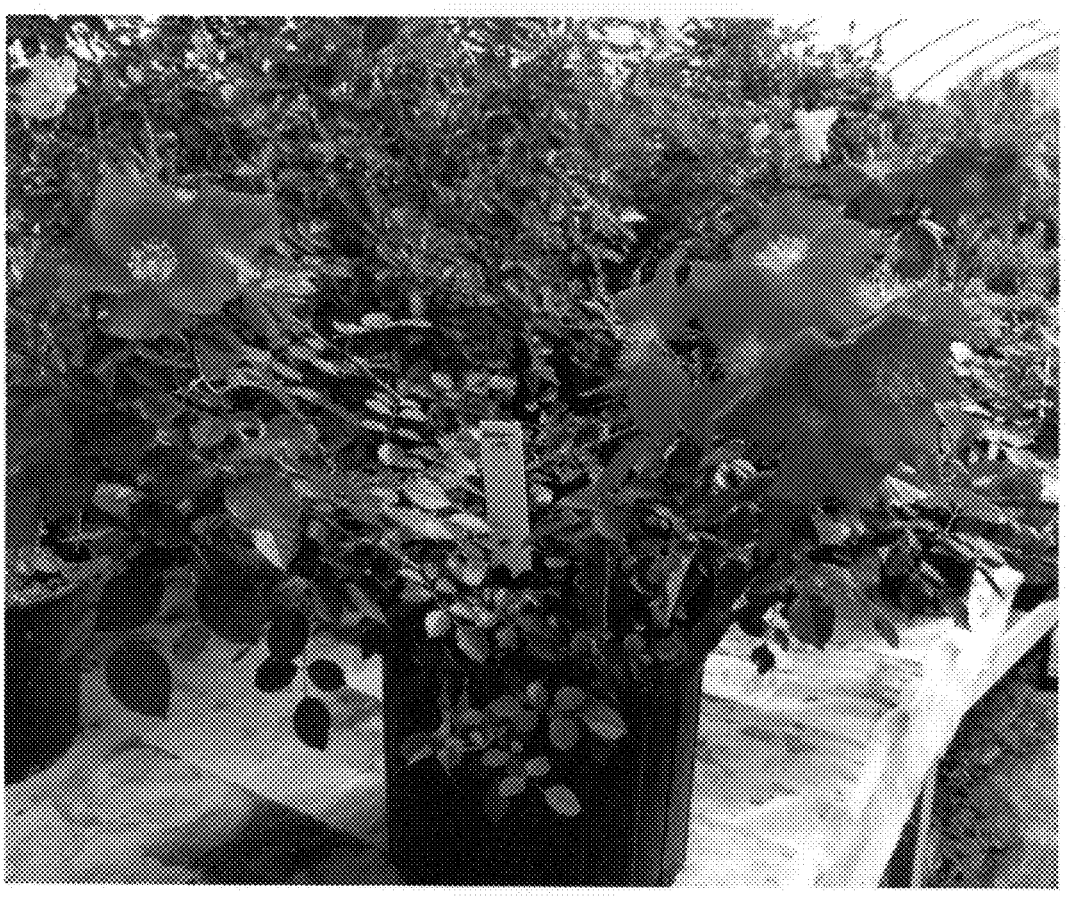
Figure 2:
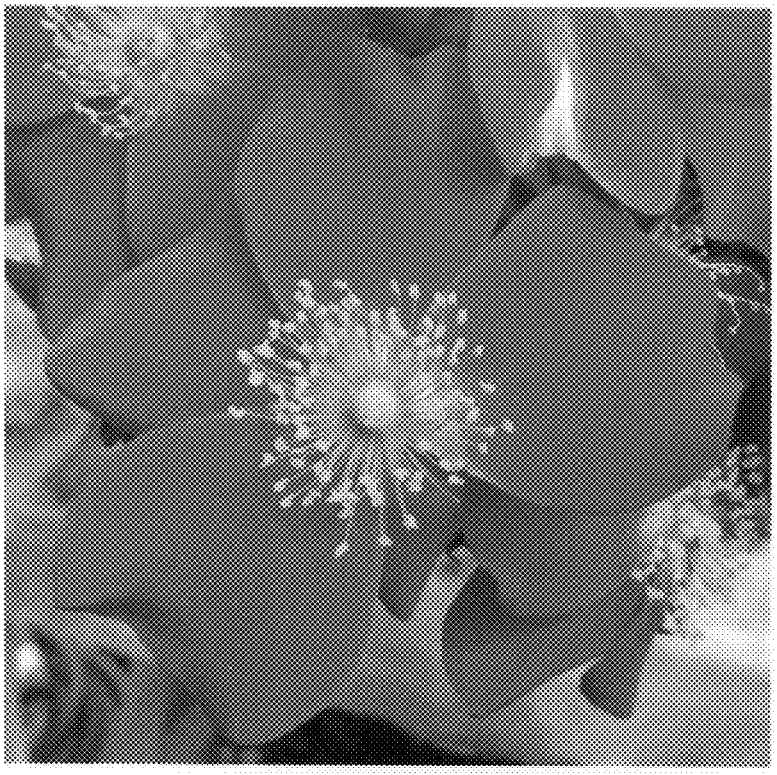

The photograph in FIG. 2 provides a close-up view of a flower of 'SFROSA159'.

Figure 3:
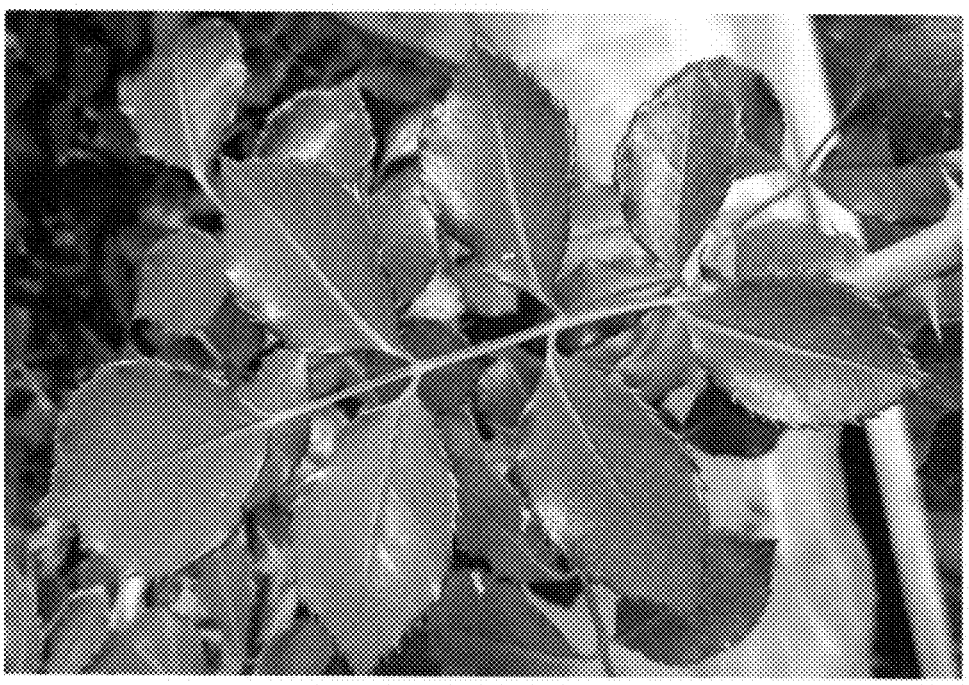

The photograph in FIG. 3 provides a close-up view of a leaf of 'SFROS159'.

The colors in the photographs are as close as possible with the photographic and printing technology utilized and the color values cited in the detailed botanical description accurately describe the colors of the new shrub rose.

DETAILED BOTANICAL DESCRIPTION

The following is a detailed description of nine month-old plants of the new cultivar as grown outdoors in 2-qt containers in Arroyo Grande, Calif. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming habit*.—Continuous bloom in California and from June to first frost in Midwestern, northeastern, and southeastern regions of the United States.

*Plant type*.—Deciduous shrub.

*Plant habit*.—Upright and compact.

*Height and spread*.—An average of 91 cm in height and width attained in one season.

*Cold hardiness*.—At least to U.S.D.A. Zone 6.

*Diseases and pests*.—Has shown tolerance to powdery mildew (*Podosphaera pannosa*) and rust (*Phragmidium mucronatum*) in California trials and tolerance to black spot (*Diplocarpon rosae*) in trials in the Midwest.

*Propagation*.—Stem cuttings.

*Time required for root development*.—An average of three weeks for root initiation with a rooted young plant produced in an average of seven weeks.

*Growth rate*.—Moderate.

Branch description:

*Stem color*.—Young; a blend of 143A to 143B and 144A, suffused with 183C maturing; a blend of 143A to 143B and 144A, lightly suffused with 183C.

*Stem surface*.—Young; glabrous, mature; slightly glaucous.

*Branching*.—1 to 3 lateral branches per stem, 1 main stem per 1-quart container.

*Stem size*.—Average of 4.5 mm in width, up to 30 cm in length.

*Thorns*.—Triangular shape, aspect slightly downward, base oval, average of 8 in number per 10 cm length stem, average of 5.5 mm in length with a base 4 mm in length and 1.5 mm in width, a blend of 161A and 183B in color.

Foliage description:

*Leaves*.—Compound, division is odd-pinnate, arrangement is alternate, average of 10.5 cm in length and 7 cm in width, internode length is an average of 2.4 cm.

*Leaflets*.—5 to 7, average of 4 cm in length and 3 cm in width, oval to ovate in shape, cuneate base, acute to rounded, serrate margins, color; emerging leaves upper surface a blend of 143A to 144C and 183B, emerging leaves lower surface a blend of 143C and 183B, young leaves upper surface 137B, young leaves lower surface 144A to 144B, mature leaves upper surface; N137A to N137B, mature leaves lower surface; 138A, pinnately veined (not conspicuous), emerging leaves upper and lower surface; glabrous and very glossy, young and mature leaves upper surface; glabrous and glossy, lower surface glabrous and dull.

*Rachis*.—Average of 4 cm in length and 1.2 mm in diameter, color; upper surface 143A to 143B suffused with 183B, lower surface 143B, rounded in shape with a center groove on upper surface, smooth upper and lower surface with a few sparse long hairs on upper surface.

*Stipules*.—Aspect outward, adnate to petiole, free apex acute in shape, average of 2 cm in length and 4 mm in width, color of upper and lower surface; 144A to 144B suffused with 183B, glabrous on upper surface and lower surface.

*Petioles and petiolules*.—Petioles; an average of 1 cm in length and 2 mm in diameter, petiolules; an average of 1.5 mm in length and 0.7 mm in diameter, petioles and petiolules; color of mature leaves upper surface 183B lightly tinged with 144A to 144B, color of mature leaves lower surface 144A to 144B, upper surface slightly pubescent and lower surface glabrous.

Inflorescence description:

*Inflorescence type*.—Single flowers borne in clusters of 5 to 8.

*Flower number*.—Continuous bloom throughout the growing season, up to eight on a stem at one time.

*Inflorescence size*.—Average of 0.5 cm in height and 7.5 cm in width dependent on air temperature.

*Flower fragrance*.—Faint.

*Flower longevity*.—5 to 8 days, depending on temperature and sunlight exposure.

*Flower type*.—Single, flat form, round in shape.

*Flower size*.—Average of 7 cm in diameter and 2.5 cm in depth (to base of reflexed sepals).

*Peduncles*.—Round in shape, average of 4 cm in length and 2.5 mm in diameter, glabrous and slightly scaberulose surface with sparse glands, 144A in color.

*Bracts*.—0 to 1, at base of peduncle, variable but typically urn-shaped base portion with elliptical leaf extension, cuneate base, an average of 4 cm in length and 1 cm in width, color matches leaf coloration on upper and lower surface, glabrous on both surfaces, margins serrate on elliptical portion and entire and glandular on basal portion.

*Flower buds*.—Conical in shape, an average of 2.5 cm in length and 1.5 cm in width prior to opening, color is 60A with very base suffused with 60D, sepals are almost horizontal and the same color as described in sepal description.

*Sepals*.—5, triangular in shape, average of 2.5 cm in length and 5 mm in width, color; 138B on upper surface and a blend of 138A and 138B on lower surface, acuminate apex with a small point leaf at apex, truncate base, reflexed on open flowers, pubescent on upper surface, slightly pubescent on lower surface, margins are pubescent with 0 to 4 lanceolate appendages; lanceolate in shape, 7 mm in length and 1 mm in width, color; N137 on both surfaces,.

*Petals*.—Average of 5 per flower, drop readily and cleanly, obcordate to rounded in shape, upper and lower surface glabrous, margins primarily with occasional crenations and slightly undulating, base broadly cuneate, apex is rounded, average of 3 cm in length and width, color; opening and fully open flowers upper surface N57A, base N57C, lower surface N57B, base N57C, fading flowers upper and lower surface; N57B, bottom of base 5B (barely fading), basal spot is absent.

*Hypanthium*.—Average of 7 mm in length and 5 mm in diameter, shiny surface, 144A in color.

*Pistils*.—Average of 16, stigma is an average of 1.5 mm in diameter and 161C in color, style is an average of 5 mm in length and 185A in color (hidden in hypanthium), ovaries are oblong in shape, 3.5 mm in length and 1.5 mm in width and 145D in color, pubescent surface.

*Stamens*.—Average of 80, filaments are an average of 1 cm in length and a blend of 17B and N163A in color, anthers are an average of 2 mm in length and 1.5 mm in width and 22A in color, pollen is moderate in quantity and 20A in color.

*Hips*.—Globose to slightly oblong in shape, an average of 2 cm in width and height, color primarily a blend of 138A and 144A with tints of 31A, surface is dull.

It is claimed:

1. A new and distinct cultivar of *Rosa* plant named 'SFROSA159' as herein illustrated and described.

* * * * *